United States Patent
Luo et al.

(10) Patent No.: US 8,202,219 B2
(45) Date of Patent: *Jun. 19, 2012

(54) ULTRASONIC BONE ASSESSMENT APPARATUS AND METHOD

(75) Inventors: Gangming Luo, Elmhurst, NY (US);
Robert S. Siffert, New York, NY (US);
William A. Johnson, Holliston, MA (US); Ronald L. Altman, Epping, NH (US); Jonathan J. Kaufman, Brooklyn, NY (US)

(73) Assignee: CyberLogic, Inc., New York, NY (US)

( * ) Notice: Subject to any disclaimer, the term of this patent is extended or adjusted under 35 U.S.C. 154(b) by 1204 days.

This patent is subject to a terminal disclaimer.

(21) Appl. No.: 11/063,012

(22) Filed: Feb. 22, 2005

(65) Prior Publication Data

US 2005/0197576 A1  Sep. 8, 2005

Related U.S. Application Data

(60) Provisional application No. 60/547,219, filed on Feb. 23, 2004.

(51) Int. Cl.
*A61B 8/00* (2006.01)
(52) U.S. Cl. ......... 600/438; 600/437; 600/439; 600/442
(58) Field of Classification Search .......... 600/437–439, 600/442
See application file for complete search history.

(56) References Cited

U.S. PATENT DOCUMENTS

| | | |
|---|---|---|
| 3,847,141 A | 11/1974 | Hoop |
| 4,361,154 A | 11/1982 | Pratt, Jr. |
| 4,421,119 A | 12/1983 | Pratt, Jr. |
| 4,774,959 A | 10/1988 | Palmer et al. |

(Continued)

FOREIGN PATENT DOCUMENTS

EP    0772999 A2    5/1997

(Continued)

OTHER PUBLICATIONS

Cheng S. et al., "Influence of Region of Interest and Bone Size in Caleaneal BMD: Implications for the Accuracy of Quantitative Ultrasound Assessments at the Calcaneous," 75 The British Journal of Radiology pp. 59-68 (2002).

(Continued)

*Primary Examiner* — Brian Casler
*Assistant Examiner* — Christopher Cook
(74) *Attorney, Agent, or Firm* — Dykema Gossett PLLC

(57) ABSTRACT

A method for the assessment of various properties of bone is provided. The method includes applying a pair of ultrasound transducers to skin on opposite sides of the bone and generating an ultrasound signal and directing the signal through both the bone to obtain a bone output signal. The method further includes establishing a set of parameters associated with the bone output signal and then further processing the parameters in order to obtain the desired bone property. Two novel parameters are also disclosed, namely the net time delay (NTD) and mean time duration (MTD) parameters. An apparatus for the assessment of various properties of bone is also provided. The apparatus includes a pair of ultrasound transducers which may be single-element transducers or array transducers in any combination. The apparatus further includes various computer hardware components and computer software for generating and directing the ultrasound signal, establishing the parameter set and performing the processing. In addition, an apparatus that is battery powered, handheld, and portable and operates in real time is also provided.

20 Claims, 5 Drawing Sheets

U.S. PATENT DOCUMENTS

| | | | |
|---|---|---|---|
| 4,913,157 | A | 4/1990 | Pratt, Jr. et al. |
| 4,926,870 | A | 5/1990 | Brandenburger |
| 4,941,474 | A | 7/1990 | Pratt, Jr. |
| 4,976,267 | A | 12/1990 | Jeffcott et al. |
| 5,040,537 | A | 8/1991 | Katakura |
| 5,054,490 | A | 10/1991 | Rossman et al. |
| 5,119,820 | A | 6/1992 | Rossman et al. |
| 5,235,981 | A | 8/1993 | Hascoet et al. |
| 5,259,384 | A | 11/1993 | Kaufman et al. |
| 5,309,898 | A | 5/1994 | Kaufman et al. |
| 5,343,863 | A | 9/1994 | Wiener et al. |
| 5,458,130 | A | 10/1995 | Kaufman et al. |
| 5,520,612 | A | 5/1996 | Winder et al. |
| 5,524,624 | A | 6/1996 | Tepper et al. |
| 5,547,459 | A | 8/1996 | Kaufman et al. |
| 5,564,423 | A * | 10/1996 | Mele et al. .................... 600/438 |
| 5,651,363 | A | 7/1997 | Kaufman et al. |
| 5,664,573 | A | 9/1997 | Shmulewitz |
| 5,749,363 | A * | 5/1998 | Ishii et al. .................... 600/453 |
| 5,752,924 | A | 5/1998 | Kaufman et al. |
| 5,785,041 | A | 7/1998 | Weinstein et al. |
| 5,785,656 | A | 7/1998 | Chiabrera et al. |
| 5,879,301 | A | 3/1999 | Chiabrera et al. |
| 5,921,929 | A | 7/1999 | Goll et al. |
| 6,027,449 | A | 2/2000 | Mazess et al. |
| 6,029,078 | A * | 2/2000 | Weinstein et al. ............ 600/407 |
| 6,090,046 | A | 7/2000 | Goll et al. |
| 6,200,266 | B1 | 3/2001 | Shokrollahi et al. |
| 6,221,019 | B1 | 4/2001 | Kantorovich |
| 6,231,528 | B1 | 5/2001 | Kaufman et al. |
| 6,234,969 | B1 | 5/2001 | Chaintreuil et al. |
| 6,251,088 | B1 | 6/2001 | Kaufman et al. |
| 6,277,076 | B1 | 8/2001 | Morris et al. |
| 6,328,695 | B1 | 12/2001 | Wammen et al. |
| 6,352,512 | B1 | 3/2002 | Wilson et al. |
| 6,364,837 | B1 | 4/2002 | Mazess et al. |
| 6,371,916 | B1 | 4/2002 | Buhler et al. |
| 6,432,057 | B1 * | 8/2002 | Mazess et al. ................ 600/449 |
| 6,436,042 | B1 | 8/2002 | Cadossi et al. |
| 6,468,215 | B1 | 10/2002 | Sarvazyan et al. |
| 6,491,635 | B1 | 12/2002 | Mazess et al. |
| 6,517,487 | B1 | 2/2003 | Mazess et al. |
| 6,520,914 | B2 | 2/2003 | Morris et al. |
| 6,585,649 | B1 | 7/2003 | Mendlein et al. |
| 6,641,537 | B2 | 11/2003 | Morris et al. |
| 6,652,473 | B2 | 11/2003 | Kaufman et al. |
| 6,740,041 | B2 | 5/2004 | Faulkner et al. |
| 6,835,178 | B1 | 12/2004 | Wilson et al. |
| 6,899,680 | B2 | 5/2005 | Hoff et al. |
| 7,285,090 | B2 * | 10/2007 | Stivoric et al. ................ 600/300 |
| 7,601,120 | B2 | 10/2009 | Moilanen et al. |
| 2001/0020128 | A1 | 9/2001 | Morris et al. |
| 2004/0052406 | A1 | 3/2004 | Brooks |

FOREIGN PATENT DOCUMENTS

| | | |
|---|---|---|
| EP | 1038501 A1 | 5/2000 |
| WO | 0028316 A1 | 5/2000 |

OTHER PUBLICATIONS

De Terlizzi, Francesca, et al. "Influence of Bone Tissue Density and Elasticity on Ultrasound Propagation: An In Vitro Study," 15 Journal of Bone and Mineral Research No. 12 pp. 2458-2466 (2000).
Dempster, D.W. "The Impact of Bone Turnover and Bone-Active Agents on Bone Quality: Focus on the Hip," 13 Osteoporosis International, pp. 349-352 (2002).
Garnero, P. et al., "Do Markers of Bone Resorption Add to Bone Mineral Density and Ultrasonographic Heel Measurement for the Prediction of Hip Fracture in Elderly Women? The EPIDOS Prospective Study," 8 Osteoporosis International pp. 563-569 (1998).
Gerdhem, Paul et al. "Biochemical Markers of Bone Metabolism and Prediction of Fracture in Elderly Women," 19 Journal of Bone and Mineral Research No. 3 pp. 386-392 (2004, published online Dec. 22, 2003).
Higuit, Ricardo Tokio et al., "Ultrasonic Densiometer Using a Multiple Reflection Technique," 49 IEEE Transactions on Ultrasonics, Ferroelectrics and Frequency Control No. 9 pp. 1260-1268 (Sep. 2002).
Kochberg, Marc C., et al. "Changes in Bone Density and Turnover Explain the Reductions in Incidence of Nonvertebral Fractures That Occur During Treatment with Antiresorptive Agents," The Journal of Clinical Endocrinology & Metabolism 87(4) pp. 1586-1592 (2002).
Mashiba, T. et al., "Effects of Suppressed Bone Turnover by Bisphosphonates on Microdamage Accumulation and Biomechanical Properties in Clinically Relevant Skeletal Sites in Beagles," 28 Bone No. 5, pp. 524-531 (May 2001).
Sarkar, Somnath et al., "Relationship Between Changes in Biochemical Markers of Bone Turnover and BMD to Predict Vertebral Fracture Risk," 19 Journal of Bone and Mineral Research No. 3 pp. 394-401 (2004, published online Dec. 22, 2003).
Wear, Keith A., "Autocorrelation and Cepstral Methods for Measurement of Tibial Cortical Thicknes," 50 IEEE Transactions on Ultrasonics, Forroelectrics and Frequency Control No. 6, pp. 655-660 (Jun. 2003).
Wuster C., et al. "Phalangeal Osteosonogrammetry Study: Age-Related Changes, Diagnostic Sensitivity, and Discrimination Power," 15 Journal of Bone and Mineral Reseaerch No. 8, pp. 1603-1614 (2000).
Ye, Shigong et al., "Ultrasound Shear Wave Imaging for Bone," 26 Ultrasound in Medicine and Biology No. 5, pp. 833-837 (2000).
Gluer, Claus-C., "Quantitative Ultrasound Techniques for the Assessment of Osteoporosis: Expert Agreement on Current Status", 12 Journal of Bone and Mineral Research No. 8 pp. 1280-1288 (1997).
Kaufman, Jonathan J. et al. "Perspectives Ultrasound Assessment of Bone", 8 Journal of Bone and Mineral Research No. 5 pp. 517-525 (1993).
McCartney, R.N. et al., "Combined 2.25 MHz Ultrasound Velocity and Bone Mineral Density Measurements in the Equine Metacarpus and their in vivo Applications", Medical & Biological Engineering & Computing (Nov. 1987) pp. 620-626.
McCartney, R.N. et al., "Transverse Path of Ultrasound Waves in Thick-Walled Cylinders," Medical & Biological Engineering & Computing (Jul. 1995) pp. 551-557.
International Search Report issued in corresponding PCT Application No. PCT/US2005/005868 (Feb. 1, 2007).
Written Opinion issued in corresponding PCT Application No. PCT/US2005/005868 (Feb. 1, 2007).
International Preliminary Report on Patentability issued in corresponding PCT Application No. PCT/US2005/005868 (Feb. 20, 2007).
Barkmann, R., et al., "Assessment of the Geometry of Human Finger Phalanges Using Quantitative Ultrasound in Vivo," 11 Osteoporosis Intl. pp. 745-755 (2000).
Haiat, G., et al,. "In Vitro Speed of Sound Measurement at Intact Human Femur Specimens," 31 Ultrasound in Medicine and Biology No. 7 pp. 987-996 (2005).
Taal et al., "Usefulness of Quantitative Heel Ultrasound Compared With Dual-Energy E-Ray Absorptiometry in Determining Bone Mineral Density in Chronic Haemodialysis Patients," 14 Nephrology Dialysis Transplantation pp. 1917-21 (1999).
Office Action (and English language translation) issued in corresponding Chinese Patent Application No. 200510071797.5 (Jun. 20, 2008).
Response to Office Action filed in corresponding Chinese Patent Application No. 200510071797.5 (Dec. 31, 2008).
Office Action (and English language translation) issued in corresponding Chinese Patent Application No. 200510071797.5 (Jun. 5, 2009).
Response to Office Action filed in corresponding Chinese Patent Application No. 200510071797.5 (Aug. 18, 2009).
Office Action (and English language translation) issued in corresponding Chinese Patent Application No. 200510071797.5 (Sep. 25, 2009).
Response to Office Action filed in corresponding Chinese Patent Application No. 200510071797.5 (Nov. 9, 2009).
Examination Report issued in corresponding European Patent Application No. 05714014.7 (issued Oct. 21, 2009).

Response to Examination Report filed in corresponding European Patent Application No. 05714014.7 (filed Apr. 30, 2010).
Examination Report issued in corresponding European Patent Application No. 05714014.7 (issued Jan. 13, 2012).
Office Action issued in corresponding Indian Patent Application No. 3459/CHENP/2006 (Jan. 2011).
Response filed in corresponding Indian Patent Application No. 3459/CHENP/2006 (Oct. 27, 2011).
Office Action issued in corresponding Indian Patent Application No. 3459/CHENP/2006 (Nov. 18, 2011).
Response filed in corresponding Indian Patent Application No. 3459/CHENP/2006 (Dec. 14, 2011).
Office Action issued in U.S. Appl. No. 12/022,720 (mailed Feb. 3, 2010).
Amendment filed in U.S. Appl. No. 12/022,720 (filed Mar. 25, 2010).
Office Action issued in U.S. Appl. No. 12/022,720 (mailed Jun. 16, 2010).
Amendment filed in U.S. Appl. No. 12/022,720 (filed Aug. 4, 2010).
Amendment filed in U.S. Appl. No. 12/022,720 (filed Nov. 11, 2010).

* cited by examiner

ULTRASONIC BONE ASSESSMENT APPARATUS AND METHOD

RELATED U.S. APPLICATION

This application claims priority to Provisional Application No. 60/547,219, filed Feb. 23, 2004, the entire disclosure of which is incorporated herein by reference.

FIELD OF THE INVENTION

The present invention relates generally to apparatus and method for non-invasively and quantitatively evaluating bone tissue in vivo. More specifically, the invention pertains to osteoporosis diagnosis and bone fracture risk assessment using multiple ultrasonic features in a battery powered portable ultrasonic device.

BACKGROUND OF THE INVENTION

In recent years, ultrasound has received a great deal of attention as a new technique for noninvasive assessment of bone, and numerous attempts have been made to use ultrasound energy for evaluating the condition of bone tissue in vivo, and thus for determining a measure of osteoporosis and assessing bone fracture risk.

In particular, Hoop discloses in U.S. Pat. No. 3,847,141 a device to measure bone density as a means for monitoring calcium content of the involved bone. A pair of opposed ultrasonic transducers is applied to opposite sides of a subject's finger, such that recurrent pulses transmitted via one transducer are 'focused' on the bone, while the receiver response of the other transducer is similarly "focused" to receive pulses that have been transmitted through the bone. The circuitry in Hoop is arranged such that filtered reception of one pulse triggers the next pulse transmission; the filtering is by way of a bandpass filter, passing components of received signals in the 25 kHz to 125 kHz range only; and the observed frequency of retriggering is believed to be proportional to the calcium content of the bone. Thus Hoop is concerned only with what he defines to be transit time for pulses in the indicated band.

Pratt, Jr. deals with establishing, in vivo, the strength of bone in a live being such as a horse. In U.S. Pat. No. 4,361,154, the inventor solves the problem posed by measuring transit time from "launch" to "reception" of pulses of 0.5 MHz and 1.0 MHz through the bone and soft tissue, and from measurement of pulse-echo time, to thereby derive a measurement of transit time through bone alone. A data bank enables the evaluation of the bone condition from the measured transit times. U.S. Pat. No. 4,913,157, also granted to Pratt, Jr., operates on the same general principle of transit time/velocity deduction, using the latter preferred frequency of 2.25 MHz as the base frequency of pulsed "launchings" and a technique of matched filtering/Fourier transform filtering for further analyzing received pulses.

Palmer et al. disclose in U.S. Pat. No. 4,774,959 a bone measurement system deriving the slope of the relation between ultrasonic frequency and attenuation of a sequence of tone signals. Being in the range of 200 kHz to 600 kHz, the signals are applied to one transducer and received by another transducer. The passage of the signals between the two transducers with and without the intervening presence of a heel bone is compared, with the assumption that the frequency/attenuation relation is a straight line, i.e., of constant slope.

U.S. Pat. No. 4,926,870 granted to Brandenburger discloses another in vivo bone analysis system which depends upon measuring transit time for an ultrasonic signal along a desired path through bone. A "canonical" waveform, determined by previous experience to be on the correct path, is used for comparison against received signals for transmission through the patient's bone, while the latter is reoriented until the received signal indicates that the bone is aligned with the desired path. Again, ultrasonic velocity through the patient's bone is assumed to have been determined from measured transit time.

Rossman et al. disclose in U.S. Pat. No. 5,054,490 an ultrasound densitometer for measuring physical properties and integrity of bone, upon determination of a transit time through bone. Alternatively, the Rossman et al. device compares absolute attenuation of specific frequency components of ultrasound signals through the bone with the absolute attenuation of the same frequency components through a medium of known acoustic properties.

Mele et al., disclose in U.S. Pat. No. 5,564,423, and in a subsequent related patent by Cadossi et al. (U.S. Pat. No. 6,436,042), disclose a device that measures the "amplitude dependent speed of sound" through a bony member in a living body. The method relies on the visual display of the received ultrasound signal, and the selection of a specific portion of the waveform for analysis.

The prior art, exemplified by the above references that have been briefly discussed, proceed on the assumptions that transit time and velocity—as well as the assumed linear slope of attenuation as a function of a set of discrete frequencies—are all-important in assessing bone. These approaches have essentially been ad hoc, with no consistent framework within which to analyze data. Despite the fact that a rich variety of information is obtainable from experiments with ultrasound (including computer simulations as well as in vitro and in vivo experiments) and that a variety of analytic results are available as well, much of the information has not been used and available, and useful aspects of the data have been ignored.

Significant steps forward in this direction have been made by Kaufman et al. (in U.S. Pat. Nos. 5,259,384 and 5,651,363) and by Chiabrera et al. (in U.S. Pat. Nos. 5,785,656 and 5,879,301). In these patents, an estimate of a "bone transfer function" associated with a given bone is obtained in a statistically optimal fashion, and parametric estimates of the phase and attenuation functions associated with it are determined. The disclosed methods also describe the use of 2D array transducers for obtaining more reproducible estimates of the bone density, architecture, and fracture risk.

Notwithstanding the advances made in the last-mentioned apparatuses and methods, there are still additional improvements needed in order to accurately and precisely assess the bone density, architecture, quality and fracture risk of a subject. While ultrasound is said to having great potential to assess the biomechanical strength of bone—since it is a mechanical wave in contrast to the ionizing radiation of standard x-ray densitometers—until now much of this potential is unrealized.

SUMMARY OF THE INVENTION

It is accordingly a primary object of this invention to provide an improved method and apparatus for characterizing and determining non-invasively the properties of bone. A more particular though not limiting object of the invention is to provide a method and apparatus for non-invasive and quantitative evaluation of bone tissue in vivo, to make accurate osteoporosis diagnosis and monitoring possible.

Another object is to meet the above object in such a way that the bone tissue evaluation and the osteoporosis diagnosis may be performed with relatively more simple and inexpensive means than those previously used.

A further object is to meet the above objects by providing more accurate and precise estimates of bone mass, architecture, bone quality, and bone strength, as compared with means disclosed previously.

A still further object is to meet the above objects by providing methods to obtain new ultrasound parameters which are sensitive to both bone mass and to architecture.

A yet further object is to provide an enhanced ability to estimate the fracture risk associated with a given living being.

As compared with the prior art, the invention incorporates information from the ultrasound measurements that is crucial to achieving the indicated objectives. In particular, the present invention is based on using neither only the time delay nor only the velocity, but a combination of parameters that is superior to the approaches disclosed in the prior art. Further, these prior approaches neither appropriately nor adequately characterize the bone being assessed, and therefore cannot meet the objectives of the present invention.

Accordingly, the present invention utilizes a new processing algorithm to capture much more information from the ultrasound measurements, to more accurately and precisely determine the characteristics of the interrogated bone—to thereby determine one or more of the bone properties such as fracture risk, strength, density, quality, and/or architecture of the bone. The advantage of such an approach is its inherent and increased sensitivity to the underlying state of the interrogated bone. This is in contrast to the prior art which cannot extract as much information on the underlying bone since they do not utilize optimal and model-based processing.

The invention in its presently preferred form of a method of non-invasive and quantitative assessment of the status of a bone tissue in vivo for one or more of the quantities: bone-mineral density, architecture, strength, quality, and fracture risk, achieves the foregoing objectives by acoustically coupling a pair of transducers to nearby skin surfaces on opposite sides of a bony member; measuring the distance separating the two transducers; generating an ultrasound excitation signal and directing this signal from one transducer to another transducer of the pair of transducers through the bone tissue, thereby producing a bone-oriented output signal, the excitation signal being a finite-duration signal repeated substantially in a range from 1 to 5000 Hz and consisting of plural frequencies spaced in an ultrasonic spectral region up to about 5 MHz; processing the output signal and distance to obtain a net time delay (NTD) parameter and a mean time duration (MTD) parameter, and further processing the two parameters to obtain an estimate of the one or more quantities.

The step of further processing may be performed with the use of one or more of a plurality of associated parameters: age, sex, fracture history, cigarette smoking history, height, and weight that is specific to an individual subject. The step of further processing may be performed with the use of multivariate linear and nonlinear regressions, a statistical hypothesis testing algorithm, and may include a neural network configured to generate an estimate of the one or more of the quantities from the parameters and from the associated parameters specific for an individual patient.

In its presently preferred apparatus form, the invention comprises transducer means including a pair of ultrasonic transducers adapted for acoustic coupling to nearby skin and for transmission through an ascertained acoustic propagation path which includes a bony part of a living body; a generator means for connecting to a transmission transducer of the pair to apply an excitation signal to the bony part, this signal being a finite-duration signal consisting of plural frequencies spaced in the ultrasonic spectral region to approximately 5 MHz and being repeated substantially in the range from 1 Hz to 5000 Hz; and a signal-processing means that are connected for response to the signal received by a receiving transducer of the pair and comprise means to provide analog-to-digital sampling and near real-time processing of the bone-oriented output signals, to thereby produce corresponding parameters and means for performing further analysis of the parameters resulting in estimates of bone properties.

In the presently preferred embodiment of the invention, an apparatus consisting of two transducers, a source transducer and a receiver transducer, are placed around a bony member of a living person, for example the heel, and adapted for acoustic coupling to the overlying skin. The apparatus is adapted to measure the distance, d, between the two transducers, and to make this information on distance available for processing. An ultrasound signal is generated and sent from the source transducer, through the heel and to the receiving transducer where it is measured and processed. The processing consists of a specialized moment-based computation, which is based on the first arriving portion of the signal. In particular, two (2) parameters are computed from the received bone-oriented signal, the net time delay (NTD) and the mean time duration (MTD) parameters, respectively. The NTD is the difference between the time delay of an ultrasound signal which was propagated through soft tissue only and the time delay of the actual bone-oriented ultrasound signal, i.e., a signal which propagated through the overlying soft tissues containing the bone tissue. It is represented mathematically as NTD=$\tau_s-\tau_b$, where $\tau_s$ is the time delay associated with a signal which had propagated through soft tissue only (but of identical overall thickness as the bony member) and $\tau_b$ is the time delay associated with a signal which had propagated through the bony member. The MTD is the time span of a given portion of the received bone-oriented signal, and is generally inversely related to the mean frequency of the signal. In the presently preferred embodiment of the invention, both the NTD and MTD are computed using only the first (half) cycle of the received signal, as the present inventors have found that the later portion of the signal is often corrupted by components having little to do with the condition of the bone tissue per se, for example multiple reflections within the overlying soft tissue. Further NTD and MTD are evaluated using a highly robust (from a statistical perspective) approach, namely computations based on zeroth, first, and second moments of the signal. Let these moments be defined, respectively, as M0, M1, and M2. It should be understood that these moments are computed over the first half cycle of the signal, and further that the moments are defined as the integral of the signal squared with respect to the product of the signal with $t^n$, where n=0, 1, 2, corresponding to M0, M1, and M2, respectively. Note that the integration is from $t_i$ to $t_f$, where $t_i$ is the start of the first half cycle and $t_f$ is the end of the first half cycle of the received bone-oriented signal. The time delay, $\tau_b$, of the received bone-oriented signal is evaluated according to $\tau_b$=M1/M0, and the time delay of the soft tissue only signal, $\tau_s$, is evaluated according to $\tau_s$=d/Vs, where d is the separation of the transducers (which is also assumed equal to the thickness of the bony member since the transducers are in contact—through a thin layer of ultrasound coupling gel—with the skin), and Vs is the velocity of ultrasound within the soft tissue. Therefore, the NTD=d/Vs−M1/M0. The MTD is evaluated according to MTD=M2/M0−$\{M1/M0\}^2$.

In the presently preferred embodiment of the invention, the bone mineral density (BMD) of the bone in the bony member is evaluated according to a linear regression between NTD and BMD, i.e., BMD=a·NTD+b. The fracture risk associated with the living person is provided by a feedforward neural network whose inputs are the ultrasound parameters NTD and MTD, and the associated parameters age, sex, weight, height and history of fracture. The output of the neural network is the probability of fracture, a number between 0 and 1.

An apparatus for the preceding embodiments is shown in FIG. 1. It should be understood that alternative functions may be utilized for estimating the BMD and fracture risk, not just a linear univariate one (for BMD) and not just a neural network (for fracture risk). For example, BMD can be evaluated using multivariate non-linear regressions, and fracture risk can be evaluated with an analytic model and statistical pattern recognition approaches which can prove useful in certain cases. It should also be appreciated that the invention as herein disclosed may be embodied using at least one of said parameter NTD and MTD.

With these and other objects and advantages in view, the present invention will be clearly understood from the ensuing detailed description in connection with the drawings.

DETAILED DESCRIPTION OF THE PREFERRED EMBODIMENT

Figure 1:
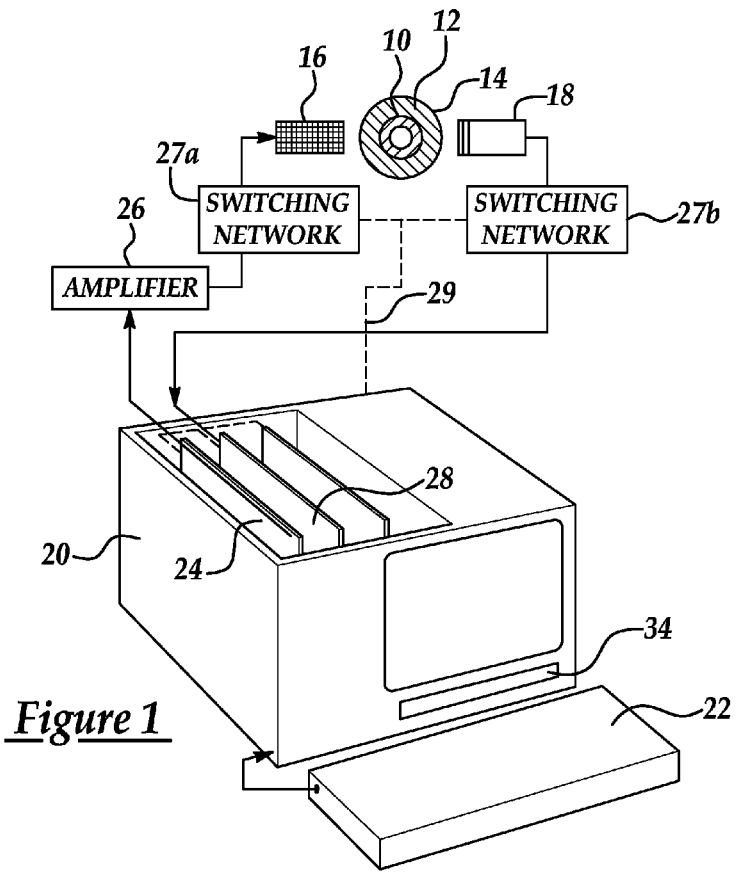
FIG. 1 is a block diagram showing the interconnections of components of an apparatus of the invention.

The invention is shown in FIG. 1 as applied to interconnected components for constructing an apparatus for practicing a method of the invention. Specifically, it is intended for non-invasively and quantitatively evaluating the status of bone tissue in vivo, as manifested through one or more of the quantities: bone-mineral density, architecture, quality, strength, and fracture risk at a given time. The components of the apparatus are, in general, commercially available from different sources and will be identified before or in the course of the detailed description of their total operation.

Referring to FIG. 1, a bone 10 to be analyzed in vivo is shown surrounded by a soft tissue 12 having an outer skin surface (skin integument) 14. The bone 10 is to be interposed between two aligned and opposed ultrasonic transducers 16 and 18, which may be identically the same, and can be obtained from Panametrics, Inc., Waltham, Mass.; suitably, each of the transducers 16, 18 may be Panametrics VIDEOSCAN part number V318-SU, having a nominal element size of ¾-inch diameter, and rated for 500 kHz. As shown, the transducer 16 is used for signal launching and the transducer 18 is the receiver for the launched signals after passing through the bone 10, its surrounding soft tissue 12, and a coupling medium such as a gel (not shown) between each transducer face and the outer skin surface 14 of the soft tissue 12. Not shown but understood to be a part of the embodiment of the invention is a sensor that is used to measure precisely and accurately the distance, d, of separation of the transducers, and it is further to be understood that this information (i.e., d) is to be made available to the processing means as described in the following paragraphs.

Basic operation is governed by a computer means 20, which may be a personal computer, such as the Dell Precision Workstation 670 available from Dell, Inc., Round Rock, Tex.; this computer contains an Intel Xeon Processor running at 3.60 GHz, with provision for keyboard instruction at 22.

An arbitrary-function generator card 24 is shown installed in the computer 20. This card is relied upon to generate an excitation signal which is periodically supplied to the launch transducer 16, via a power amplifier means 26. The power amplifier 26 is suitably the Model No. 240L, an RF power-amplifier product of EIN, Inc., Rochester, N.Y. This amplifier provides a 50 dB gain, over the range 20 kHz to 10 MHz. In addition to power amplifier means 26, the excitation signal must pass through a switching network 27a in an alternative embodiment using multi-element, linear- or two-dimensional array transducers, described fully infra.

The excitation signal generated by the card 24 is a finite-duration pulse that is repeated substantially in the range from 1 to 5000 Hz. The card 24 may suitably be a waveform synthesizer, a product of PC Instruments, Inc., Lawrence, Kans., identified by PC Instruments part No. PCI-341. The waveform synthesizer provides generation of analog signals independent of the host computer 20, that allows full processor power to be used for other tasks, including calculation of waveform data.

Another card 28 is shown installed into the computer 20 for converting signals received at the receiving transducer 18 into a digital format for further processing in the computer 20. The card 28 may suitably be a 200 MHZ 14 bit waveform digitizer, a part known as Compuscope 14200, a product available from Gage Applied Technologies, Inc., of Montreal, Quebec, Canada.

As with the launch transducer 16, in an alternative embodiment described more fully infra, where receiving transducer 18 is a multi-element, linear or two-dimensional array transducer, a switching network 27b must be placed between the receiving transducer 18 and the card 28 of computer 20.

Also, general signal-processing/display/storage software, for the signal processing control and operation of the computer 20 is not shown but will be understood to be loaded at CD drive 34 into the computer 20; this software is suitably MATLAB for Windows, available from The Math Works, Inc., Natick, Mass. Further software, also not shown but loaded into the computer 20, are the Neural Network and Optimization Toolboxes, also from The Math Works as well as software (drivers) for interfacing the cards in the computer, available from Gage Applied Technologies and PC Instruments. In addition, a Visual C++ compiler, preferably one available from Microsoft Corporation (Redmond, Wash.) is also understood to be loaded into the computer 20.

In the presently preferred embodiment, involving the described components of FIG. 1, the same components are utilized not only for performing the continuously updated averaging of the latest succession of signals received at the receiving transducer 18 after they have passed through a bone member 10-12-14, but also for establishing and entering into computer storage the data of a reference signal that is obtained by removing the body member 10-12-14 from the space between the transducers 16, 18 and replacing it with a medium with known acoustic properties, such as water, and known path length. This latter signal is useful for calibrating a device so that, e.g., different devices produce the same NTD and MTD values when measuring the same object (either a calibration object or a bony member). It may also be used in the computation of a "bone transfer function," as described fully in U.S. Pat. Nos. 5,259,384, 5,651,363, 5,785,656, and 5,879,301 and which are all incorporated by reference hereinto.

Figure 2:
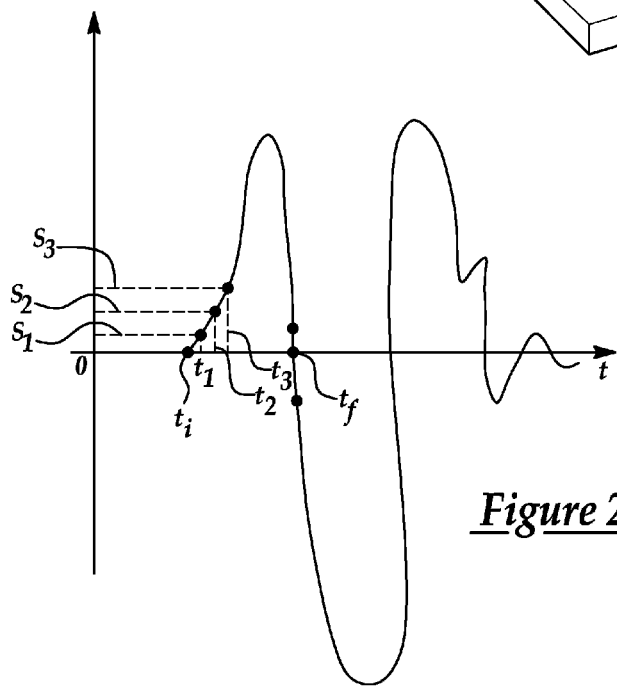
FIG. 2 is a graphical description of a part of the signal processing utilized in a presently preferred embodiment of the invention.

In this embodiment, as may be understood the two transducers consist of a first transducer and a second transducer acoustically coupled to nearby skin on opposite sides of a bony member (i.e., bone tissue surrounded by overlying soft tissue). The arbitrary-function generator card 24 and power amplifier 26 are used to produce an electrical input signal which is applied to the first transducer. This causes an ultrasound signal to be generated and directed from the first transducer to the second transducer through the bone tissue to obtain a bone-oriented output (received) signal. The bone-oriented output signal is then digitized using the A/D card 28 and processed to obtain an estimate of at least one of parameter net time delay and parameter mean time duration. The net time delay (NTD) and mean time duration (MTD) parameters are defined through use of a set of signal moments M0, M1, and M2. It should be understood that these moments are computed over the first half cycle of the signal. The first half cycle is identified automatically according to an algorithm (program) stored within the computer means 20. The algorithm first computes noise statistics, i.e., the mean ($\mu_n$) and standard deviation ($\sigma_n$) of the noise-only portion of the received bone-oriented output signal, using standard statistical techniques (see for example the book *Statistics Manual* by Crow, Davis and Maxfield, published by Dover Publications, Inc., New York, in 1960, and which is incorporated by reference hereinto); this noise-only portion occurs at the earliest times of the received signal, that is before the ultrasound signal propagating through the bony member has reached the receiving (second) transducer. Once the noise statistics are evaluated, the initial time point, $t_i$, of the first half cycle of the bone-oriented output signal is identified. With additional reference to FIG. 2, the identification of initial time point, $t_i$, is obtained by searching for a first set (that is the earliest in time of occurrence of said set) of three consecutive signal values, $s_1$, $s_2$, and $s_3$, associated with times $t_1$, $t_2$, and $t_3$, respectively, such that $s_1 - \mu_n > 2 \cdot \sigma_n$, $s_2 - \mu_n > 8 \cdot \sigma_n$, and $s_3 - \mu_n > 16 \cdot \sigma_n$. It should be understood that $t_i$ is chosen as one sampling interval less than $t_1$. Next the final time point, $t_f$, of the first half cycle is identified. This is done by searching the values of the output signal (from which the mean, $\mu_n$, has been subtracted) from smaller times to greater times (starting at time $t_i$) for the first occurrence of a change in sign, that is the identification of two adjacent signal values of opposite sign. The final time point, $t_f$, is evaluated by linear interpolation of the two adjacent signal values; $t_f$ is the value at which the linear interpolation (i.e., the straight line between the two adjacent signal points) is zero (again, with additional reference to FIG. 2). Following the identification of the times $t_i$, $t_f$, the moments are then evaluated. The moments are defined as the integral of the product of the signal squared with $t^n$, where t is time and n=0, 1, 2, corresponding to M0, M1, and M2, respectively. Note that the integration is from $t_i$ to $t_f$, where $t_i$ is the start of the first half cycle and $t_f$ is the end of the first half cycle of the received bone-oriented signal. The time delay, $\tau_b$, of the received bone-oriented signal is evaluated according to $\tau_b = M1/M0$, and the time delay of the soft tissue only signal, $\tau_s$, is evaluated according to $\tau_s = d/Vs$, where d is the separation of the transducers (which is also assumed equal to the thickness of the bony member since the transducers are in contact—through a thin layer of ultrasound coupling gel—with the skin), and Vs is the apparent velocity of ultrasound within the soft tissue. Therefore, the NTD=d/Vs−M1/M0. The MTD is evaluated according to MTD=M2/M0−{M1/M0}$^2$.

In the presently preferred embodiment of the invention, the bone mineral density (BMD) of the bone in the bony member is evaluated with further processing according to a linear regression between NTD and BMD, i.e., BMD=a·NTD+b. The values a and b in the linear regression are evaluated by a method of least squares, and using independently measured values of BMD; in the presently preferred embodiment, the independent measure of BMD is obtained with a dual energy x-ray absorptiometer (PIXI, GE Medical Systems, Madison, Wis.). It should however be understood that an estimate of BMD may be obtained not only using NTD, but may include MTD as well.

A fracture risk associated with the living person is computed by a feedforward neural network whose inputs are the ultrasound parameters NTD and MTD, and the associated parameters age, sex, weight, height, degree of bone turnover, and history of fracture. The output of the neural network is the probability of a future fracture, a number between 0 and 1. Neural network is an information processing device that utilizes a large number of simple modules which are highly interconnected with one another. Neural networks are well known in the art (the reference can be made to *Neural Networks, A Comprehensive Foundation*, by Simon Haykin, IEEE Press, Macmillan College Publishing Company, New York, 1994). They are appreciated for their remarkable ability to derive meaning from complicated or imprecise data and are usually used to trace trends that are too complex to be noticed by either humans or other computer techniques.

It should be understood that a multivariate linear regression, a multivariate nonlinear regression, or even a statistical hypothesis testing algorithm may be used to estimate bone mineral density using at least one of the ultrasound parameters, NTD and MTD. Furthermore, the computation of one or more of said quantities BMD, bone strength, bone fracture risk, bone architecture and bone quality may be derived using at least one parameter as may be derived from the acoustic bone transfer function (in either the frequency and time-domains, or in both), and may also include at least one of said parameter net time delay and parameter mean time duration, and may further include a set of other parameters related to the living being, namely, thickness of the bony member, age, sex, height, weight, history of fracture, cigarette smoking history, degree of bone turnover, and family history of fracture. It should be understood that the degree of bone turnover can be measured in a number of ways, including but not limited to blood analysis and urine analysis. Note also that the nonlinear regression may be implemented with a neural network.

It is useful to provide some additional background as to the relationship between NTD and bone-mineral density. (Again, this density is in fact an areal density—not a true volumetric density—and is also therefore equivalent to total bone mass or overall bone thickness.) For this it is useful to model the bony member as consisting solely of two layers, one bone layer of thickness $d_{bl}$, and another soft tissue layer of thickness $d_{sl}$; the thickness, d, where $d = d_{bl} + d_{sl}$, is equal to the overall thickness of the bony member. It should be understood that the soft tissue layer includes not only the overlying soft tissues but all the soft tissues located in the path of an ultrasound wave, for example, including the soft tissues within the marrow spaces of any trabecular bone that may be part of the bony member. It should further be understood that the bone tissue layer includes all of the bone located in the path of an ultrasound wave, and that it has been effectively compressed into a single layer. In this model, then, the time delay of the bone-oriented signal is $\tau_b$, where $\tau_b = \tau_{bl} + \tau_{sl}$, and $\tau_{bl}$ is the time for propagation through the pure bone layer, and $\tau_{sl}$ is the time for propagation through the pure soft tissue layer. The expression can then be written, using $\tau_{bl} = d_{bl}/v_{bl}$, and $\tau_{sl} = d_{sl}/v_{sl}$, where $v_{bl}$ and $v_{sl}$ are the speed of propagation of ultrasound through bone and soft tissue, respectively, as $d/v_{sl} - \tau_b = d_{bl}(v_{bl} - v_{sl})/(v_{bl} \cdot v_{sl})$. In this expression, $d_{bl}$ is the parameter of interest, namely (directly proportional to) the total bone mass or bone-mineral density (BMD) of the bony member and the other parameters, namely $v_{bl}$ and $v_{sl}$ can, as the present inventors have discovered, be treated as constants. Therefore, recognizing that $d/v_{sl} - \tau_b$ is the net time delay, it should then be appreciated that NTD is proportional to the BMD. It should be also understood that although this model is, strictly speaking, applicable only to a "two layer system," the inventors have discovered that it works well in bony members comprised mostly of cortical bone and even in bony members that have mostly trabecular bone, and in bony members which have substantial amounts of both kinds of bone tissue. Finally, it is important to point out that although the NTD was computed using a time delay of a bone-oriented signal and the bony member thickness, it is possible to use any two (2) of three (3) ultrasound parameters to estimate BMD and obtain similar results as with NTD based on time delay and thickness, the three parameters being (1) time delay, $\tau_b$, of the bone-oriented signal; (2) the thickness, d, of the bony member (assumed equivalent to the distance separating the two transducers); and (3) the velocity, v ($=d/\tau_b$), of the signal through the bony member. In addition then, to the relationship between NTD and BMD, it may be understood that BMD is proportional also to tau·(a1−b1·v) and also d·(a1/v−b1), where a1, a2, b1, and b2 are constant regression coefficients, and thus should be considered to be equivalent to the net time delay parameter. It should also be understood that while in the presently preferred embodiments of the invention the time delay of the bone-oriented signal is computed with the method of moments, other approaches could be used in estimating NTD. These methods could include, but not be limited to selection of the time delay based on when the signal first rises above the noise level, or the time when the signal first reaches 5 percent of its maximum value. Thus the present invention should be understood to include any methods which can estimate a time delay of the bone-oriented signal. However, the presently preferred method for determining the time delay based on moments has been discovered to be remarkably resistant to the effects of noise. Further, it should be appreciated that the evaluation of velocity, v, is best achieved through use of a method of moments as well, using the expression $v = d/\tau_b$, where $\tau_b$ is computed based on the method of moments, as in the presently preferred embodiment of the invention, although other methods for measuring time delay (and hence velocity) can be used as well, as described in the material hereinabove. It should further be appreciated that although the moments in the presently preferred embodiment rely on the square of the signal in their computation, the present inventors have found that other exponents have proven to have good performance also, for example just the signal itself (exponent=1), and thus all exponents should be considered to be within the scope of the invention. Further, it should be appreciated that the use of most of the first cycle (through the integration of the signal with respect to the various powers of time, t) is a key aspect of the present invention as it is responsible for the superior performance obtained, and therefore the use of the majority of the first cycle in determining time delay of the signal is to be understood to be a major feature of the invention. This would also be understood to include curve fitting a model of the signal to obtain a value for the time delay, as well as various weighting functions and also to include any nonlinear functions as well.

The invention pertains to the non-invasive ultrasound assessment of bone, including the assessment of bone strength, density, architecture, quality, and fracture risk. Since ultrasound propagation through bone depends on both mass (BMD) and architecture (as well as material properties per se), it is useful to combine multiple ultrasound measurements in order to uniquely identify bone properties. In an alternative embodiment of the invention, ultrasound measurements are made from at least two (2) directions, and the information combined in order to more accurately identify bone properties. In an alternative embodiment, ultrasound is propagated in the phalanges (fingers) from 2 directions approximately orthogonal to one another. Then two (2) sets of data, namely two (2) net time duration parameters and two (2) mean time duration parameters are measured and combined in a multivariate regression to output the bone mineral density and architecture of the finger bone. It should be understood than a variety of ultrasound parameters may be used in addition to the NTD and MTD parameters, such as parameters associated with a set of at least two (2) acoustic transfer functions associated respectively with at least two (2) directions of propagation through the bone, as well as the set of at least two (2) bony member thicknesses associated, respectively, with the at least two (2) directions of propagation through the bone, as well as a set of other parameters related to the living being, namely, age, sex, height, weight, history of fracture, cigarette smoking history, degree of bone turnover, and family history of fracture. It should be further understood that this alternative embodiment of the invention may be used on any bone within a living body in which multi-directional ultrasound measurements can be obtained, not just the phalanges, and further that the multidirectional measurements need not necessarily be in directions that are approximately orthogonal with one another, but may also be oblique as well.

There are, however, many bones for which such multidirectional data cannot be obtained. In these cases, another embodiment is preferred. In this alternative embodiment, ultrasound measurements are acquired from a single direction; however the measurements are carried out at 2 sharply distinct frequencies. In a present embodiment, a single transducer acting as a source emits two signals, one signal with a center frequency of 100 kHz, and the other signal with a center frequency of 2.1 MHz. A receiving transducer, also capable of receiving both signals, namely a broadband receiver having a bandwidth of 50 KHz-2.1 MHz measures the two signals and evaluation of a pair of quantitative data is obtained. In a present embodiment, the pair of data is the NTD and MTD, each measured using the said two distinct frequency input signals, respectively. The multi-frequency data serves as an alternative to the multidirectional data, and also leads to improved accuracy in estimating the aforesaid bone related properties.

It should be understood that any quantitative ultrasound parameters (e.g., NTD, MTD, velocity, etc.) can be measured using one of the above embodiments, that is, in a multidirectional embodiment, or a multi-frequency embodiment. It should also be understood that a number of ways can be utilized to generate multidirectional data and multi-frequency data, including the same transducer pair and rotating them (e.g., 90 degrees) to obtain the multidirectional data set, or two different pairs of transducers, arranged or configured to operate in two orthogonal directions (or any oblique direction), multi-frequency transducer pair, or different transducer pairs operating at distinct frequencies, for example. Any means for generating multi-frequency or multidirectional ultrasound data should be considered to be within the scope of the present invention. Also, the preferred frequency differential should be substantial, not less than at least 50%, but 100% or more is preferable. In the previously described multi-frequency embodiment, the differential is 100%×(2100 kHz–100 kHz)/100 kHz=2000%. Further, the multidirectional data should be understood to also include the use of arrays, which allows for oblique propagation between the two transducers. It should also be appreciated that only one of the two transducers may be an array, with the other being a single element.

As yet further advances over the prior art, in yet an alternative embodiment of the invention, concentric or annular phased arrays are used. Either the transmitter, receiver, or both, may be an annular phased array; if only one is an annular array, then it is to be understood that the other transducer is a single element transducer. The annular array is operated to focus into a given region the ultrasound beam; thus a number of bone properties may be determined, corresponding to the spatial regions which are ultrasonically interrogated. Because of the heterogeneity of bone, knowledge of the bone properties (or equivalently, the ultrasound parameters) in the scanned regions leads to an overall much more accurate estimate of overall bone density, architecture, strength, quality and/or fracture risk. The prior art has relied on rectangular 2D arrays, which lead to very expensive systems (due to both high cost of 2D arrays and the large number of source excitation elements required). The annular array overcomes these shortcomings and is well described in Chapter 10 of the excellent reference *Medical Imaging Systems* by Albert Macovski, published by Prentice-Hall, Inc. in Englewood Cliffs, N.J., in 1983, and which is incorporated by reference hereinto. The annular array can be phased so that cylindrical "slices" of the bone can be scanned, using dynamic focusing, and thus is far superior to prior methods.

Another useful embodiment relies on a phase insensitive transducer receiver to measure the received waveform after it has been transmitted through a bony member. The phase insensitive nature of the receiver allows attenuation dependent measurements to be made much more accurately as compared to the phase sensitive transducers normally used. A number of different ways are available by which phase insensitive measurements can be obtained, using specialized single element transducers, or array transducers using absolute amplitudes and summing together the voltages from each of the elements of the array. It should be understood that the invention includes any way by which phase insensitive measurements may be obtained, and the use of any of a number of ultrasound parameters that may be obtained from the phase insensitive receiver measurements.

Figure 3:
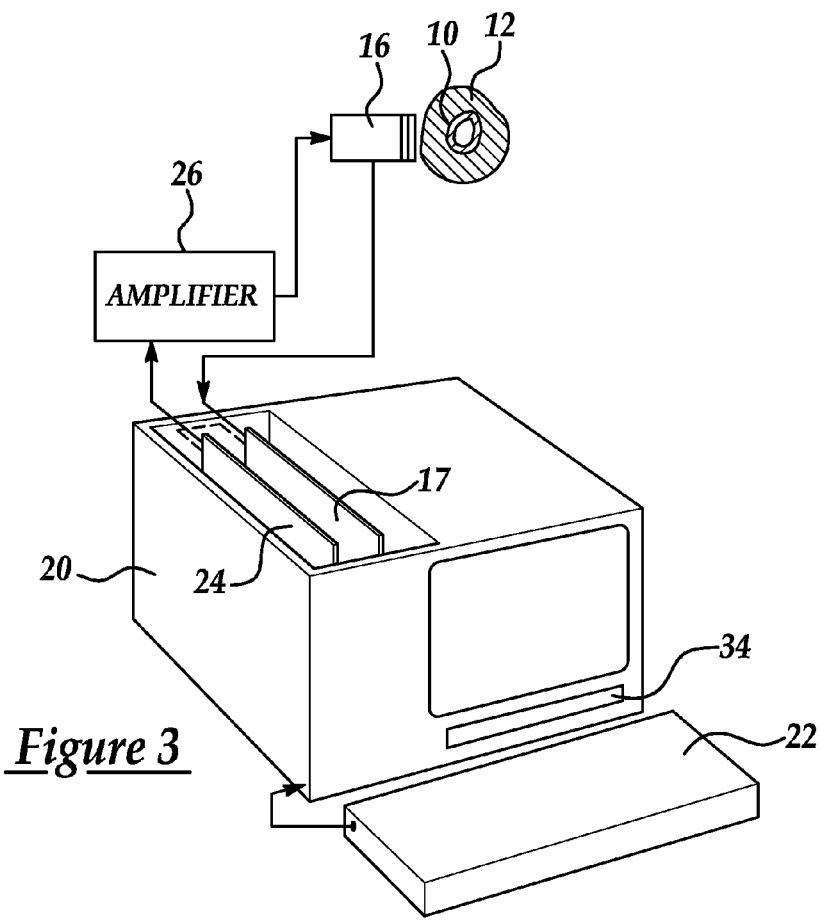
FIG. 3 is a block diagram of an alternative embodiment of the invention.

In yet one further embodiment of an invention to assess bone, a single transducer 16 is used in reflection mode. In this embodiment, and as shown in FIG. 3, an ultrasonic pulser-receiver card 17 can be added to a computer 20; the pulser-receiver card can be suitably a Matec Instruments, Inc., of Northborough, MA, Model No. SR-9000. It should be understood that in this embodiment of the invention, one end of a buffer rod (not shown in FIG. 3) made of Lucite (and of known acoustic properties) is placed in contact with the skin overlying a bone to be ultrasonically assessed, and the transducer 16 is placed onto the other end of the buffer rod. An acoustic wave is generated by the transducer 16, and propagates through the buffer rod towards the skin and bone. At each change of acoustic impedance, Z, (i.e., Z=the product of volumetric density and velocity of ultrasound for a given propagation medium), a portion of the propagating wave is reflected back and transmitted forward. In this case, the wave is thus partially reflected and partially transmitted at the buffer rod-skin interface, at the skin-cortical bone interface, and the cortical bone-trabecular bone interface, and so forth and so one. (In practice, reflections from further interfaces—for example from the trabecular bone-cortical interface at the far end of the bony member—would not be measurable above noise. However, the processing of these deeper measurements should be considered to be within the scope of the present invention, in the instances where sufficient signal-to-noise ratios can be obtained.) The reflections from these interfaces are used to obtain information about the bone tissue. In a presently preferred embodiment of the invention, a 7.5 MHz ultrasound pulse is used in a pulse-echo mode configuration. Knowledge of the acoustic properties of the plastic buffer rod and of the soft tissue (skin) is assumed, although it is possible to measure both independently. The reflection of the wave from the soft tissue-cortical bone interface is measured by the transducer 16 operating in pulse-echo mode. The relative amplitude, R, of the reflected signal (relative to the incoming wave) is given by $R=(Zcb-Zst)/(Zcb+Zst)$, where Zcb is the acoustic impedance of the cortical bone and Zst is the acoustic impedance of the soft tissue, assumed known. Thus by simply measuring the amplitude, R, of the reflected wave relative to the amplitude of the signal impinging on the outer cortical surface, the acoustic impedance, Zcb, of the cortical bone can be determined by $Zcb=Zst(1+R)/(1-R)$. In addition to measuring the reflection from the near surface of the cortical bone, the reflection from the cortical-trabecular bone interface is measured as well. In this embodiment, the time delay, $\tau_{cb}$, between the signal reflected from the soft tissue-cortical bone interface and the cortical-trabecular bone interface is measured. The areal bone mineral density, $BMD_{cb}$ [in units of kg/m$^2$], of the cortical-only portion of the bony member is computed as $BMD_{cb}=\rho_{cd}d_{cd}=\rho_{cb}V_{cd}d_{cb}/v_{cb}=Zcb\tau_{cb}/2$. Thus in this embodiment of the invention a direct measurement of the areal bone density of the cortical only portion of the bony member (on the side nearest the transducer) is made. Several additional points should be noted with respect to this alternative embodiment of the invention. First, it should be appreciated that although the areal bone mineral density of the cortical bone is estimated using the acoustic impedance of the cortical bone, the acoustic impedance itself is of important diagnostic value, as it is the product of true density and velocity, which both decrease in osteoporosis. Thus acoustic impedance is a strongly sensitive measure of the bone loss disease process. Second, although a very high frequency waveform was used to be able to isolate the reflections from each of the interfaces, it is also possible to use a lower frequency waveform and to consider for the occurrence of multiple reflections as well. This can be done by a direct analysis based on reflected waves in a layered medium. In this case, an overall transfer function is derived relating the input waveform to the received (reflected) waveform. The transfer function depends on the acoustic properties and thicknesses associated with the soft tissue, cortical bone and trabecular bone, respectively. These properties are estimated using least-squares in either the frequency or time domain, and in this way extremely short time (high frequency) waveforms are not required, and multiple reflections (for example from within the cortical bone layer) can also be handled. Thus, it should be also recognized that not only properties of the cortical bone can be estimated, but the acoustic impedance of the trabecular bone can be estimated as well. It should also be appreciated that the frequency-dependent attenuation associated with the cortical bone can be estimated as well. It should also be appreciated that the length of the buffer rod would generally be chosen so that multiple reflections from within the rod are able to be time-windowed out. The frequency and duration of the interrogating signal will also generally be chosen to minimize overlapping of echoes, but this is not strictly speaking necessary. For example, it should be understood that the response to overlapping echoes can be evaluated and used to solve for the parameters of interest. (See for example, the book *Optimal Seismic Deconvolution*, by Jerry M. Mendel, published by Academic Press, New York, in 1983.) It should further be appreciated that a reference measurement can be made by operating the transducer with the buffer rod attached in a medium with known acoustic properties, such as in air or in water; in this way knowledge of the source waveform can be obtained and the effect of the buffer rod on the propagating waveform can also be accounted for. It should also be appreciated that a number of different ultrasound transducers and pulsers can be utilized in the various embodiments of this invention. For example, a single element transducer operating in pulse-echo mode with a pulser-receiver is the most common embodiment. However, a dual element transducer can also be used, in which the transmitting and receiving elements are both electrically and acoustically distinct; this can often simplify the measurement of the received waveform. It should therefore be appreciated that any transducer/pulser configuration can be considered to be within the scope of the present invention, and further that both analog and digital embodiments, or a combination of both, should be considered to be within the scope of the present invention. It should also be recognized that because of the relatively thin nature of the soft tissue, it may be useful to "extend" it by using a buffer rod with acoustic properties matched as closely as possible to the soft tissue. It should also be appreciated that although the acoustic impedance expressions utilized herein are for a lossless and dispersionless medium, it would be straightforward to extend them and the entire analysis to the lossy and dispersive case, and thus should be considered to be within the scope of the present invention. Finally, it should also be appreciated that because of the non-planar and oblique nature of the cortical surface on which the ultrasound wave impinges, the amplitude of the reflected wave may not be related solely to acoustic impedance differences. Thus in such a case it should be understood that the transducer may be angled (either physically or through phasing of an array) in a plurality of directions in order to correct for the non-planarity and obliqueness of the cortical surface. In a present embodiment, the transducers are angled continuously and the system outputs the maximum value of the reflected amplitudes for subsequent processing.

An additional embodiment of the invention is to operate a pair of transducers in both through transmission and pulse-echo mode; in this way, two sets of ultrasound parameters may be obtained, namely that set associated with the transmission measurements, and that set associated with the reflection measurements. It should be understood that these data sets may be further processed, using linear or nonlinear, univariate or multivariate regressions, to obtain one or more of the aforementioned bone properties.

Figure 4:
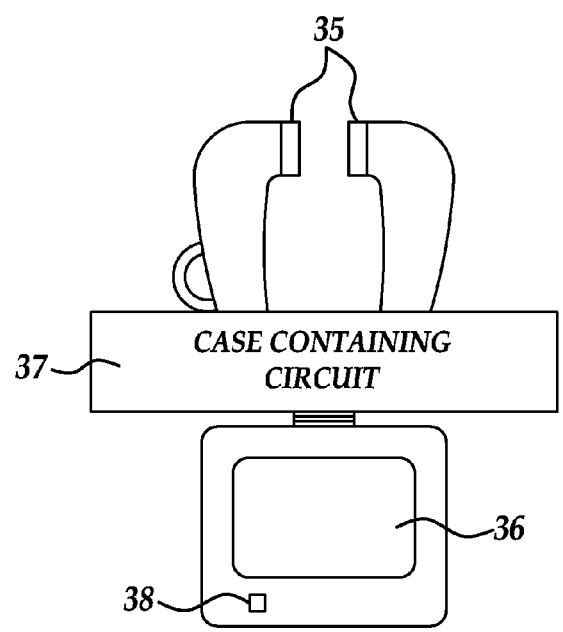
FIG. 4 is a drawing of another embodiment of the invention.

A further alternative embodiment of the invention is shown in FIG. 4. In this embodiment, near real-time processing is used to compute a set of parameters associated with the ultrasound waveform, namely the NTD and MTD. These parameters may then be used for estimating bone density, strength, architecture, quality and fracture risk through a multivariate linear or nonlinear regression, neural network or other pattern classification method (see for example H. L. van Trees, *Detection, Estimation and Modulation Theory*, Vol. 1, John Wiley and Sons, incorporated by reference hereinto). In order that each device provides similar outputs, a digital filter simulating the effects of the bony member and bone tissue tissue may be used on the reference signal of each manufactured device (which because of small variations in the various components will be somewhat different). This can serve as a convenient way to calibrate or standardize each device. (An alternative and useful calibration—and simpler approach—is to measure known reference materials and include device specific constants to ensure that each device outputs the same values when measuring the same material object.) This filter can be minimum phase or linear phase, or some other phase which has been shown to be a good model for bone tissue; it can have a linear, quadratic or other power or combinations of powers attenuation function. The device can extract out the net time delay and mean time duration parameters directly, as disclosed hereinabove, or alternatively indirectly by using, for example, the velocity and attenuation functions of a transfer function estimated from the received signal and a reference signal which has propagated through a medium of known acoustic properties, which in this preferred alternative embodiment is water. Another alternative embodiment of the indirect approach for extracting the net time delay and mean time duration parameters is to use a set of digital filters to filter the source waveform (e.g., a reference waveform which had propagated through water only, corrected for the known time delay and which includes the effects of both the source and receiving transducers, and the source excitation signal) with a respective set of given attenuations and phases, to produce a set of simulated (or "bone-oriented") output signals. In this alternative embodiment, a set of pairs of simulated net time delay and mean time duration parameters are computed from the set of simulated output signals, and are stored within each device, together with the associated pair of values of phase and attenuation. It should be understood that this allows for the use of a look-up table or other similar means (e.g., surface response modeling and interpolation techniques) well known in the art, to equate the measured (i.e., on an actual subject) net time delay and mean time duration parameters to an equivalent pair of attenuation and phase values. This embodiment is particularly useful for correcting for differences that might arise due to variations between transducers that produce differences in ultrasound waveforms; this might then lead to differences in computed ultrasound parameters, without that is, the use of such a correction scheme as disclosed herein.

Figure 5:
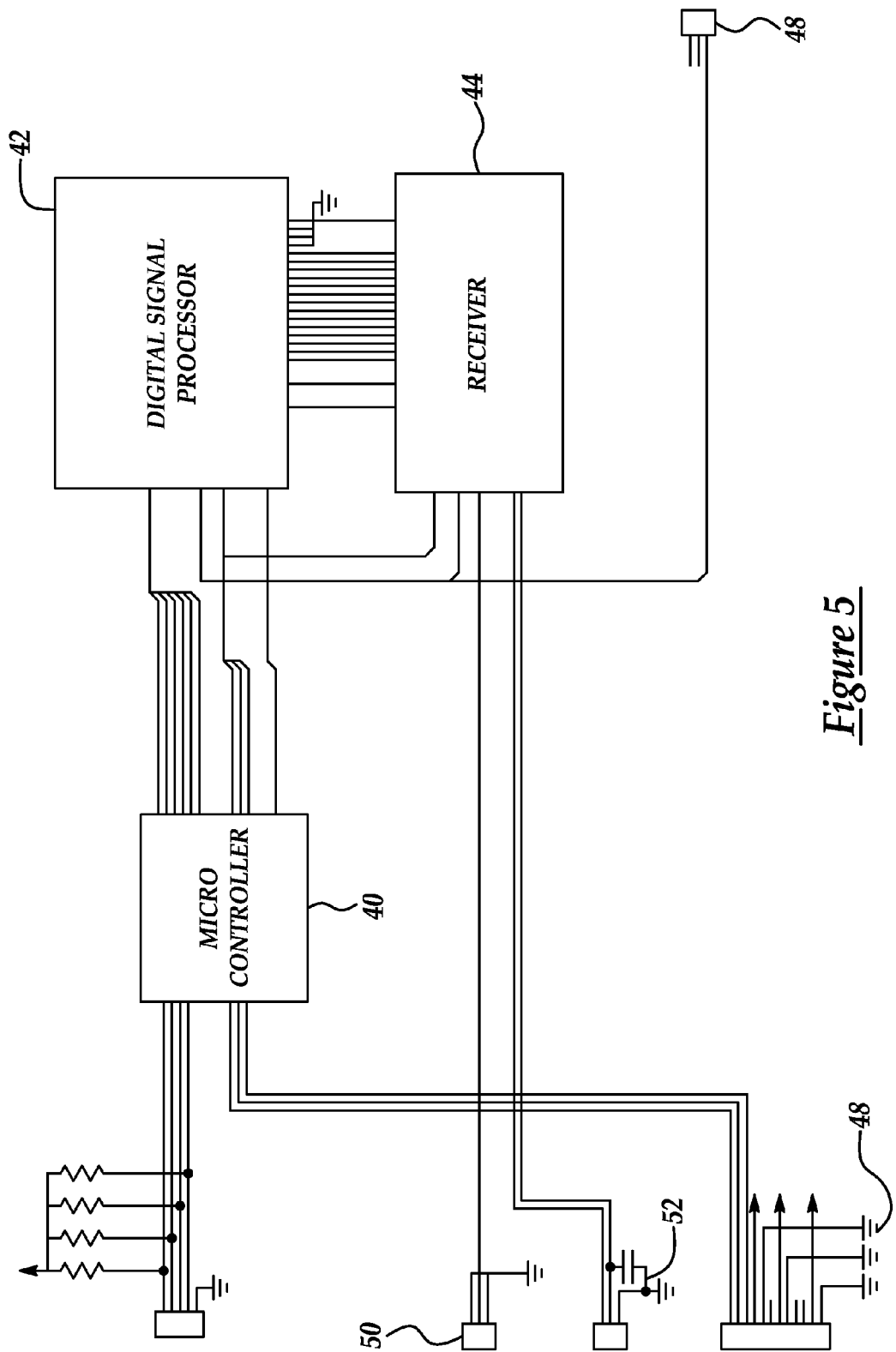
FIG. 5 is a schematic diagram of the interconnected electronic components for the embodiment of FIG. 4.
Figure 6:
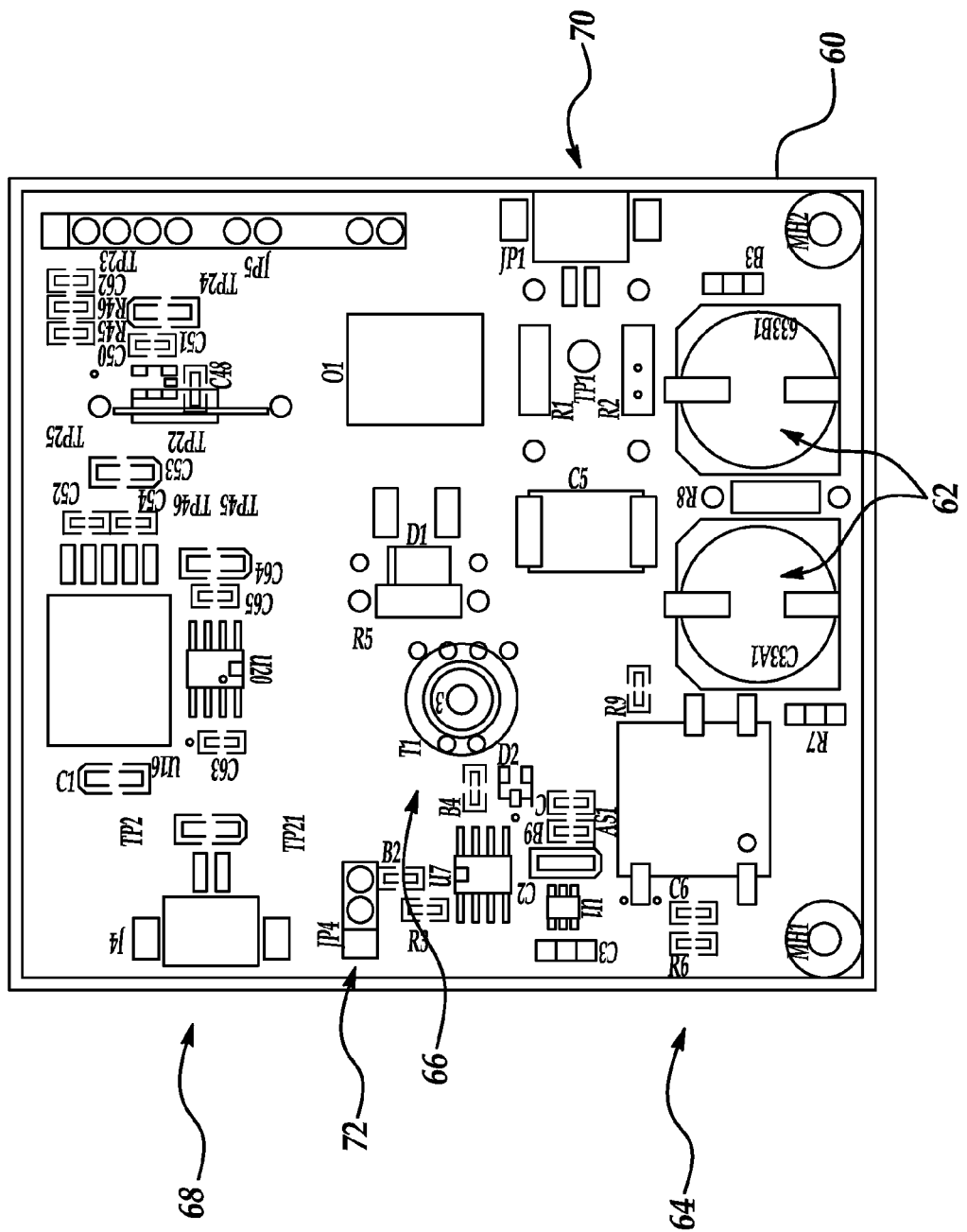
FIG. 6 is a printed circuit board schematic of the pulser and power components for the embodiment of FIG. 4 and FIG. 5.

An overall schematic diagram is shown in FIG. 4, and contains two transducers 35, a touch-screen display 36, an on-off switch 38, and a case 37 which contains the required circuitry and distance measuring hardware. In this alternative preferred embodiment, the required circuitry is placed on two (2) printed circuit boards (PCB's), although in some other embodiments only one (1) may be preferred. The present embodiment has a pulser/system power board and a receiver/processing board. A schematic diagram showing the interconnected components of this embodiment of the invention is shown in Fig.5. As may be seen, the apparatus consists of a microcontroller 40, a digital signal processor 42, a receiver containing an analog to digital converter 44, as well as connections for pulser board input 46, pulser board output 48, receiver transducer output 50, and distance measurements 52. The PCB for the pulser/system power components is shown in FIG. 6. As may be seen the pulser/power board 60 contains high voltage capacitors 62, a high voltage inverter 64, a trigger transformer 66, as well as provisions for inputting battery power 68, for outputting transducer excitation signal 70, for powering the receiver/processing board, and for receiving signals from the receiver/processing board. Of special significance to note is that the pulser output 70 is digitally controlled in terms of a pulse width and repetition rate signal from the receiver/processing board (not shown) connected at 72. It should also be noted that in this alternative embodiment the receiver board measures the distance (through a distance sensor (also not shown) between the transducers each time an averaged set of waveforms is obtained; this distance measurement is "paired" with the receiver measurement in order for the net time delay parameter to be properly computed. It should also be understood that the distance sensor may be based on a number of techniques, including but not limited to digital encoders, micrometer based encoding, linear variable differential transformers, among others.

The key features of the device (besides its near real-time nature) are: (i) portability; (ii) handheld; (iii) battery-powered; and (iv) a display that provides feedback for the operator. Capability for entering a subject's age, sex, height, weight, degree of bone turnover, and other patient specific factors are also included. The device may also be connected to a computer, a "Palm Pilot," or a printer, or any combination of the above; this connection may be wired or wireless (e.g., Bluetooth). The device in a present embodiment also has a touch screen, to allow convenient control of certain aspects of its operation. One way the device may be used is to display to the operator the received waveform; when the waveform has a given shape, the operator pushes a button on the device which initiates an averaging and data storage operation. This can also be done automatically, without user intervention. As another way of using the device, the operator moves the device slowly over the skin, acquiring a range of parameter values associated with the specific anatomical site being measured. The device processes this set or sets of parameter values in order to obtain an optimal and reproducible estimate of bone strength, density, architecture, quality, and fracture risk. For example, the device may use a maximum likelihood estimate based on the probability distribution (histogram) associated with a given parameter. It should be understood that in order to maximize the utility of the device that the display may have the option of being able to rotate. In one such embodiment, the display can rotate ±90°. In another embodiment, the display can also be angled up or down, either in addition to rotating or instead of. The ability to adjust the position of the display improves the ability of the user to operate the device, and also to apply it in different ways to one or more anatomical sites in a living body. In one presently preferred embodiment of the invention, the user places the device on a bony member a specified number of times (5 in this alternative embodiment) and the device outputs the minimum as the estimate of the parameter of interest, in this preferred alternative embodiment the minimum BMD.

It should be appreciated that the invention may include the use of a template for improving the reproducibility of the measurement. Although the region to be measured is located generally without the help of a template, the template can be also used after the ultrasound measurement to make a record of the location used for a given subject. This information is then used the next time the subject is measured; the template is used to mark the skin where the measurement was carried out previously, allowing for example, treatment to be monitored since the same site is measured each time. It should be understood that the template approach can be used on a variety of anatomical sites, including but not limited to the heel. The use of a template is important because of the large amount of heterogeneity of the bones comprising a living body. It should be further understood that a variety of templates and locating devices could be devised and used in the manner as described in this paragraph to reproducibly locate and measure a specific region of interest.

In another embodiment of the invention, transducers 16 and 18 in FIG. 1 are multi-element, two-dimensional array transducers. In a presently preferred embodiment, each transducer 16, 18 is rectangular, 3 cm by 4 cm, comprised of 10×13(−2)=128 elements (two corner elements not being used), with nominal center frequency of 850 kHz and bandwidth 80%. As mentioned supra, the excitation signal generated by card 24 serves as input to power amplifier means 26. The output of power amplifier means 26 then passes through switching network 27a before reaching transducer 16. Signals received at transducer 18 must similarly pass through switching network 27b before card 28 receives them. Switching network 27a is a signal routing and measurement switch which sequentially connects the single channel output of the waveform generator card 24 via power amplifier means 26 to each of the elements of the launch transducer 16. Switching network 27b similarly connects the single channel input of card 28 to each of the elements of the receiving transducer 18. Networks 27a and 27b may be assumed to be under computer control via a general purpose interface bus (GPIB) 29, shown as a dashed line in FIG. 1.

This alternative embodiment with an array or with two arrays allows a predetermined anatomical landmark to be reliably located automatically through the use of signal/image processing rather than by physically repositioning the transducers 16 and 18 relative to the anatomical region. The anatomical landmark can, for example, be the edge of a heel bone. Locating such a landmark can be accomplished because the parameters disclosed in the present invention are strongly dependent on the type of tissue (e.g., soft tissue vs. bone) through which the ultrasound signal is propagated. For example, the net time delay is much lower (close to zero) when the ultrasound signal travels through the soft tissue laterally surrounding the bone as compared to the bone itself (typically 1-5 microseconds). By locating anatomical landmarks in this fashion, that is through acquisition of an image rather than a single number, improved reproducibility and precision in ultrasound parameter estimates can be accomplished. In one preferred embodiment, data obtained through the ultrasonic interrogation of the tissue—for example through identification of a region of minimal bone density—can itself be used as local reference sites for reproducibly positioning the tissue relative to the transducers 16 and 18. The above embodiments utilizing "electronic" positioning can be implemented using suitable template matching and correlative techniques, as well as edge detection algorithms, well known in the art and as described in the book *Digital Image Processing*, by Gonzales and Wintz, 2d ed. (1981), Addison-Wesley, Redding, Mass. which is fully incorporated hereinto by reference. It should be understood that all of the techniques disclosed herein including but not limited to linear and nonlinear uni- and multivariate regressions, neural networks, pattern recognition, statistical hypothesis testing, pulse echo and through transmission ultrasound techniques (including but not limited to multi-directional and multifrequency methods), and all of the parameters disclosed herein, including, but not limited to mean time duration, net time delay, velocity, attenuation, acoustic transfer function, acoustic impedance, and bony member thickness, are directly applicable and useful and preferred for use with multi-element, two-dimensional array transducers.

The utilization of multi-element, two-dimensional array transducers 16 and 18, also allows the averaging of a large set of data from a plurality of excitation signals which can lead to more accurate estimates of bone density, strength, and fracture risk, and also improve the capacity for reliable intra-patient and inter-patient comparisons. Furthermore, each element of each transducer 16, 18 can be operated in pulse-echo mode, enabling the soft tissue thicknesses overlying a bone to be measured, and the acoustic impedance and BMD to be estimated—at a multiplicity of spatial locations—as well. For this purpose an ultrasonic pulser-receiver card can be added to the computer 20. The pulser-receiver card can be suitably a Matec Instruments, Inc., of Northborough, Mass., Model No. SR-9000.

In an alternative embodiment, the multi-element, two-dimensional array transducers 16 and 18 can be utilized in a synthetic array aperture mode. In this mode a single excitation signal is passed through a plurality of the array elements, also known as the aperture. By moving the entire aperture one element at a time across the array, high resolution images are made possible, but a high signal to noise ratio can also still be maintained and beam divergence reduced. For this embodiment, the switching networks 27a and 27b may suitably be a relay-based system, for example Model No. JX/256 manufactured by Cytec Corp. of Penfield, N.Y. Additional information which may be useful in this approach is *Synthetic Aperture Radar*, by Curlander and McDonough, John Wiley, 1991, the entire disclosure of which is incorporated herein by reference.

In yet another alternative embodiment, only one of transducers 16, 18 is an array transducer—preferably transducer 18. In this single-array transducer embodiment, transducer 16 may be a 1 MHZ nominal frequency 1.5 inch diameter transducer, Model No. 392, from Panametrics, Inc. of Waltham, MA while transducer 18 may be a 850 kHz nominal center frequency, 3 cm×4 cm rectangular array transducer having 128, 3 mm×3 mm elements from Acoustic Imaging of Phoenix, Arizona. In general, transducer 16 should be large enough to cover a region which is of clinical interest and which may also include some anatomical landmarks to be used in repositioning transducer 16. Transducer 18 should be approximately the same size as transducer 16, although the size and shape of the transducers relative to each other may vary. Nevertheless, transducers 16 and 18 should overlap in a region sufficiently large to obtain enhanced reproducibility and accuracy. With respect to the heel region, such a region may be several centimeters in size. However, other anatomical sites, such as a finger, may utilize a smaller region of overlap. Finally, because transducer 16 is a single-element transducer, switcher 27a is not required in the single-array transducer embodiment.

The single-array transducer embodiment is much easier to implement and is much less expensive than the dual-array embodiment described hereinabove, yet retains most of the advantages of the dual-array embodiment, in terms of enhanced reproducibility and accuracy, as compared to embodiments employing a pair of single-element transducers. It should be understood that the single-array transducer embodiment, like the dual-array transducer embodiment, can be used with a variety of signal processing techniques, including mean time duration and net time delay. It should also be understood that, depending on the signal processing technique utilized, the single-array transducer embodiment may or may not include means for, or the step of, directing the ultrasound signal through a known medium to obtain a reference electrical output signal.

It should be appreciated that while this invention applies to bony members generally in a living being, certain bones which have shown to be well suited for ultrasound examination have been identified. They include, for example, the calcaneus (the heel bone), the phalanges (finger bones), the radius (wrist), and any of the long bones for cortical bone assessment (for example, the tibia and femur, particularly the proximal femur or hip).

Figure 7:
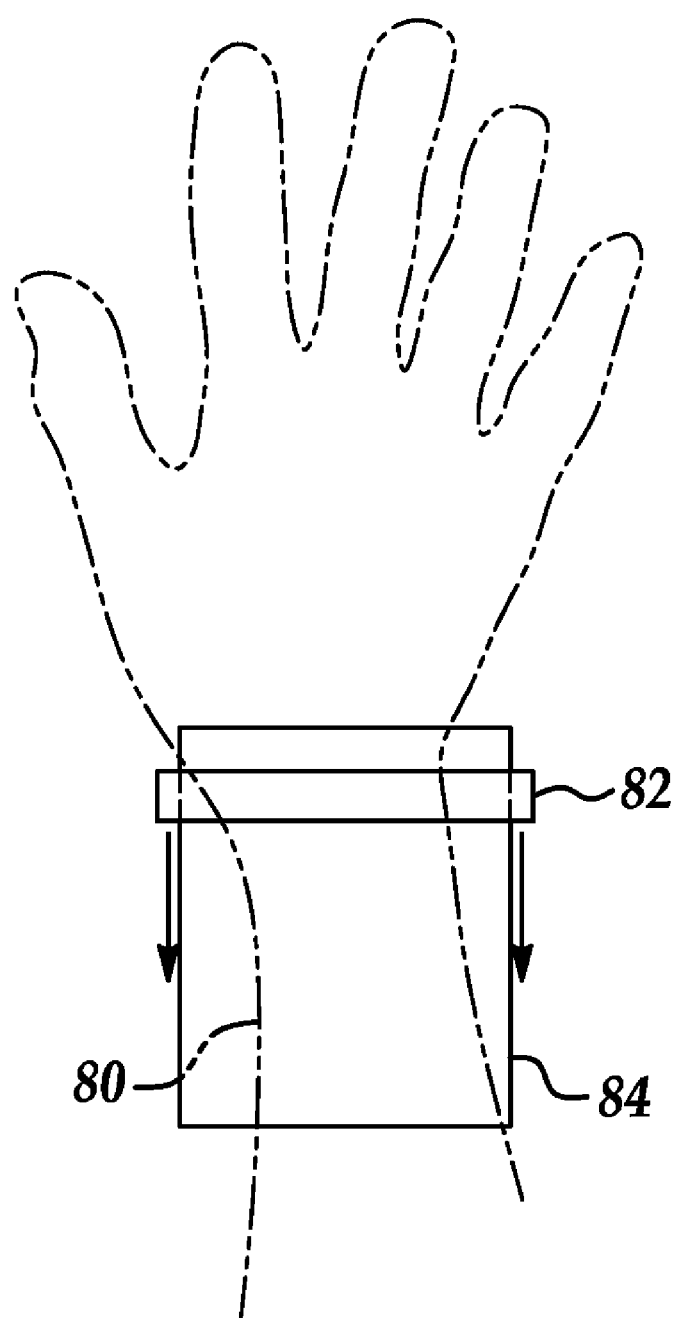
FIG. 7 is a diagram of an alternative embodiment of the invention.

In one additional embodiment of the invention, and with additional reference to FIG. 7, the distal radius (not shown) of an individual's arm (wrist) 80 is ultrasonically interrogated using the methods and techniques as disclosed herein. An apparatus consisting of a linear array receiver transducer 82 (in the presently preferred alternative embodiment it contains 20 elements, with each rectangular element having a width of 2.5 mm and a length of 5 mm, being 5 cm overall in length, and nominally operating with a 3.5 MHz center frequency) and a large single element rectangular (5 cm×10 cm) transmitter transducer 84 is used, with the array transducer 82 oriented longitudinally in a direction substantially orthogonal to a longitudinal axis of the arm. In this embodiment, the wrist of a living being is subjected to ultrasound interrogation generated by the rectangular transducer, propagates through the wrist (using coupling gel on both transducers to assure good transmission and reception), and is measured at the other side by the linear (1D) array transducer. In the present embodiment, the data from each element of the array is processed (the processing hardware is not shown in FIG. 7 but is understood to be similar to that shown either in FIG. 1 or FIGS. 4-6) to obtain the net time delay and mean time duration parameters. The array is moved (translated) proximally under computer control (not shown) using stepper motors so that a length of about 10 cm is scanned at the distal portion of the wrist at a prescribed set of discrete spatial steps (in the present embodiment each step is 2.0 mm, making for a total of 50 steps). The ultrasound data is stored in conjunction with the x,y coordinates with which it is associated, so that an image of the wrist (and more specifically the radius) showing the NTD parameter (or any of the ultrasound parameters disclosed herein) can be displayed. This image is used to reproducibly identify, through further processing, a comparable region of interest, using standard imaging techniques well known in the art image processing and of bone densitometry in general. This would include for example, acquiring ultrasound data not just of the radius per se but also of surrounding soft tissue only regions. The value of bone mineral density for the individual is then evaluated from the automatically identified region of interest, and output. It should be understood that the disclosed apparatus and method for determination of the condition of one or more of the bone properties bone mineral density, bone architecture, quality, strength and fracture risk of the radius can be embodied in a number of ways that have been disclosed herein. This includes but is not limited to, for example, use of a 1D transmitting array in addition to the receiver array (in which case the transmitter would also be translated along the arm), use of a single element transmitting transducer of approximately the same overall dimension as the 1D receiver array (again in which case the transmitter would also be translated along the arm), use of phasing of the array or arrays to achieve at least one of focusing and deflection, and the use of 2D array or arrays to avoid the need for mechanical scanning. In addition, any of the approaches disclosed hereinabove, including but not limited to evaluation of net time delay, mean time duration, attenuation, velocity, bony member thickness, and acoustic transfer function, as well as multi-directional and multi-frequency methods, may be utilized in the non-invasive ultrasound assessment of the radius. Note finally that the use of an array or arrays in any of the embodiments of the invention usually would be understood to lead to a plurality of ultrasound parameters, for example a plurality of net time delay parameters, which would be further processed to extract or obtain the estimate desired, namely one or more of the bone properties bone mineral density, bone architecture, quality, strength and fracture risk.

It should also be understood that the methods and apparatus disclosed herein can be used to estimate one or more of the said bone quantities, namely, bone density, bone quality, bone architecture, fracture risk, and bone strength not only of the bony member being ultrasonically interrogated, but also at a site anatomically remote to that site, for example, the hip and spine.

While several embodiments of the present invention have been disclosed hereinabove, it is to be understood that these embodiments are given by example only and not in a limiting sense. Those skilled in the art may make various modifications and additions to the preferred embodiments chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

What we claim is:

1. A method of non-invasive and quantitative assessment of the status of bone tissue in a bony member in vivo for at least one of the quantities, bone-mineral density, bone strength, bone fracture risk, bone architecture and bone quality comprising the steps of:
   acoustically coupling a first transducer and a second transducer to nearby skin on opposite sides of said bony member;
   measuring a distance between said first transducer and said second transducer;
   generating an ultrasound signal and directing said ultrasound signal from said first transducer to said second transducer through said bone tissue to obtain a bone-oriented output signal;
   processing said bone-oriented output signal and said distance, whereby an estimate of at least one of a net time delay parameter and a mean time duration parameter is obtained, said net time delay parameter determined responsive to a comparison between a time for said ultrasound signal to travel between said first and second transducers and an estimated time for said ultrasound signal to travel through soft tissue over said distance and said mean time duration parameter determined responsive to a time span of a predetermined portion of said bone-oriented output signal; and
   further processing said at least one of said net time delay parameter and said mean time duration parameter, whereby an estimate of said at least one of the quantities, bone-mineral density, bone strength, bone fracture risk, bone architecture and bone quality is obtained.

2. The method of claim 1 wherein said step of processing said bone-oriented output signal and said distance includes use of a method of moments, said moments computed over a first half cycle of said bone-oriented output signal.

3. The method of claim 1 wherein said bony member is a heel.

4. The method of claim 3 wherein at least one of said first transducer and said second transducer is an array transducer.

5. The method of claim 1 wherein said bony member is a forearm and wherein at least one of said first transducer and said second transducer is an array transducer.

6. The method of claim 1 wherein said bony member is a finger.

7. The method of claim 6 wherein at least one of said first transducer and said second transducer is an array transducer.

8. The method of claim 1 wherein said further processing step includes the substep of obtaining said estimate responsive to a regression of said at least one of said net time delay parameter and said mean time duration parameter.

9. The method of claim 1 wherein said bony member is an arm.

10. The method of claim 1 wherein said at least one of a net time delay parameter and a mean time duration parameter comprises both of said net time delay parameter and said mean time duration parameter.

11. An apparatus for non-invasive and quantitative assessment of the status of bone tissue in a bony member in vivo for at least one of the quantities, bone-mineral density, bone strength, bone fracture risk, bone architecture and bone quality comprising:
   first and second transducers including means for acoustically coupling said first and second transducers to nearby skin on opposite sides of said bony member;
   means for generating an ultrasound signal and directing said ultrasound signal from said first transducer to said second transducer through said bone tissue to obtain a bone-oriented output signal;
   means for measuring a distance between said first transducer and said second transducer;
   means for processing said bone-oriented output signal and said distance, whereby an estimate of at least one of a net time delay parameter and a mean time duration parameter is obtained, said net time delay parameter determined responsive to a comparison between a time for said ultrasound signal to travel between said first and second transducers and an estimated time for said ultrasound signal to travel through soft tissue over said distance and said mean time duration parameter determined responsive to a time span of a predetermined portion of said bone-oriented output signal; and
   means for further processing said at least one of said net time delay parameter and said mean time duration parameter, whereby an estimate of said at least one of the quantities, bone-mineral density, bone strength, bone fracture risk, bone architecture and bone quality is obtained.

12. The apparatus of claim 11 wherein said means for processing said bone-oriented output signal and said distance includes use of a method of moments, said moments computed over a first half cycle of said bone-oriented output signal.

13. The apparatus of claim 11 wherein said bony member is a heel.

14. The apparatus of claim 11 wherein at least one of said first transducer and said second transducer is an array transducer.

15. The apparatus of claim 11 wherein said bony member is a forearm and wherein at least one of said first transducer and said second transducer is an array transducer.

16. The apparatus of claim 11 wherein said bony member is a finger.

17. The apparatus of claim 16 wherein at least one of said first transducer and said second transducer is an array transducer.

18. The apparatus of claim 11 wherein said further processing means includes means for obtaining said estimate responsive to a regression of said at least one of said net time delay parameter and said mean time duration parameter.

19. The apparatus of claim 11 wherein said bony member is an arm.

20. The apparatus of claim 11 wherein said at least one of a net time delay parameter and a mean time duration parameter comprises both of said net time delay parameter and said mean time duration parameter.

* * * * *